United States Patent [19]
Collins et al.

[11] Patent Number: 5,902,917
[45] Date of Patent: May 11, 1999

[54] ALKYLAROMATICS PRODUCTION

[75] Inventors: Nick A. Collins, Fall Branch, Tenn.; Dominick N. Mazzone, Wenonah; Chaya R. Venkat, Princeton, both of N.J.

[73] Assignee: Mobil Oil Corporation, Fairfax, Va.

[21] Appl. No.: 08/980,108

[22] Filed: Nov. 26, 1997

[51] Int. Cl.⁶ ............... C07C 1/00; C07C 2/64; C07C 2/68; C07C 5/22
[52] U.S. Cl. .......... 585/323; 585/315; 585/316; 585/449; 585/467; 585/475
[58] Field of Search .................. 585/310, 315, 585/316, 319, 323, 449, 467, 475

[56] References Cited

U.S. PATENT DOCUMENTS

| | | | |
|---|---|---|---|
| 3,200,163 | 8/1965 | Fenske | 260/671 |
| 3,751,504 | 8/1973 | Keown et al. | 260/672 |
| 4,169,111 | 9/1979 | Wight et al. | 585/323 |
| 4,459,426 | 7/1984 | Inwood et al. | 585/323 |
| 4,857,666 | 8/1989 | Barger et al. | 585/323 |
| 4,870,222 | 9/1989 | Bakas et al. | 585/323 |
| 4,891,458 | 1/1990 | Innes et al. | 585/323 |
| 5,149,894 | 9/1992 | Holtermann et al. | 585/467 |
| 5,177,285 | 1/1993 | Van Opdorp et al. | 585/467 |
| 5,453,554 | 9/1995 | Cheng et al. | 585/467 |

OTHER PUBLICATIONS

*Catalysis of Organic Reactions*, Mobil/Badger Ethylbenzene Process—Chemistry and Catalytic Implications, pp. 39–50, by Francis G. Dwyer.

*Primary Examiner*—Glenn Caldarola
*Assistant Examiner*—Thuan D. Dang
*Attorney, Agent, or Firm*—Peter W. Roberts; Malcolm D. Keen

[57] ABSTRACT

There is provided a process for producing alkylaromatics, especially ethylbenzene and cumene, wherein a feedstock is first fed to a transalkylation zone and the entire effluent from the transalkylation zone is then cascaded directly into an alkylation zone along with an olefin alkylating agent, especially ethylene or propylene.

9 Claims, 1 Drawing Sheet

ALKYLAROMATICS PRODUCTION

BACKGROUND OF THE INVENTION

There is provided a process for producing alkylaromatics, especially ethylbenzene and cumene, wherein a feedstock is first fed to a transalkylation zone and the entire effluent from the transalkylation zone is then cascaded directly into an alkylation zone along with an olefin alkylating agent, especially ethylene or propylene.

Ethylbenzene is a valuable commodity chemical which is currently used on a large scale industrially for the production of styrene monomer. Ethylbenzene may be produced by a number of different chemical processes but one process which has achieved a significant degree of commercial success is the vapor phase alkylation of benzene with ethylene in the presence of a solid, acidic ZSM-5 zeolite catalyst. In the commercial operation of this process, the polyalkylated benzenes, including both polymethylated and polyethylated benzenes are recycled to the alkylation reactor in which the reaction between the benzene and the ethylene takes place. By recycling the by-products to the alkylation reaction, increased conversion is obtained as the polyethylated benzenes (PEB) are converted to ethylbenzene (EB). In addition, the presence of the PEB during the alkylation reaction reduces formation of these species through equilibration of the components because at a given feed composition and under specific operating conditions, the PEB recycle will reach equilibrium at a certain level. This commercial process is known as the Mobil/Badger process and is described in more detail in an article by Francis G. Dwyer, entitled "Mobil/Badger Ethylbenzene Process-Chemistry and Catalytic Implications", appearing on pages 39–50 of a book entitled *Catalysis of Organic Reactions,* edited by William R. Moser, Marcel Dekker, Inc., 1981.

Ethylbenzene production processes are described in U.S. Pat. Nos. 3,751,504 (Keown), 4,547,605 (Kresge), and 4,016,218 (Haag); reference is made to these patents for a detailed description of such processes. The process described in U.S. Pat. No. 3,751,504 is of particular note since it includes a separate transalkylation step in the recycle loop which is effective for converting a significant proportion of the more highly alkylated products to the desired ethylbenzene product. Other processes for the production of ethylbenzene are disclosed in U.S. Pat. Nos. 4,169,111 (Wight) and 4,459,426 (Inwood), in both of which a preference for large-pore size zeolites such as zeolite Y is expressed, in distinction to the intermediate-pore size zeolites used in the processes described in the Keown, Kresge and Haag patents. U.S. Pat. No. 3,755,483 (Burress) describes a process for the production of ethylbenzene using zeolite ZSM-12 as the alkylation catalyst.

Ethylbenzene (EB) can be synthesized from benzene and ethylene ($C_2=$) over a variety of zeolitic catalysts in either the liquid phase or in the vapor phase. An advantage of a liquid phase process is its low operating temperature and the resulting low content of by-products. For example, U.S. Pat. No. 4,891,458 describes the liquid phase synthesis of ethylbenzene with zeolite Beta.

To minimize polyalkylation and other undesirable side reactions, production of such alkylaromatics as ethylbenzene and cumene typically operates with high ratios of aromatic (e.g., benzene) to alkylating agent (e.g., ethene) in the feed to the alkylation reactor. Zeolite-catalyzed processes generally operate at aromatic/olefin (A/O) molar feed ratios of three or above, while processes catalyzed by $AlCl_3$ or supported phosphoric acid often operate at A/O's of three and below. However, in both cases polyalkylated aromatics (e.g., diethylbenzenes) are produced at levels that prohibit simply disposing of them as waste. These polyalkylated aromatics are instead reacted further with feed aromatic to form additional monoalkylate via transalkylation reactions. In the case of zeolite-catalyzed alkylaromatic processes, this transalkylation may take place in the alkylation reactor (as in the case of the Mobil/Badger process discussed above) or may take place in a separate transalkylation reactor, with the effluent from the transalkylation reactor being combined with the alkylation reactor effluent and sent to product recovery.

SUMMARY OF THE INVENTION

There is provided a process for producing an alkylbenzene selected from the group consisting of ethylbenzene and cumene, said process comprising the steps of:

(a) introducing a feed into a transalkylation zone, said feed comprising benzene and polyalkylbenzene selected from the group consisting of polyethylbenzenes and polypropylbenzenes, the molar ratio of benzene to polyalkylbenzene in said feed being in excess of one, said feed being essentially free of ethylene and propylene, wherein said transalkylation zone comprises a transalkylation catalyst;

(b) contacting said feed with said transalkylation catalyst under sufficient transalkylation conditions to produce an effluent from said transalkylation zone comprising monoalkylbenzene and benzene;

(c) introducing (i) the entire effluent from the transalkylation zone and (ii) an alkene selected from the group consisting of ethylene and propylene into an alkylation zone comprising an alkylation catalyst; and (d) contacting said effluent from said transalkylation zone and said alkene with said alkylation catalyst under sufficient alkylation conditions to produce an effluent from said alkylation zone comprising monoalkylbenzene and polyalkylbenzenes, wherein the point of first introduction of alkene is downstream from the transalkylation zone.

DETAILED DESCRIPTION OF THE INVENTION

Figure 1:
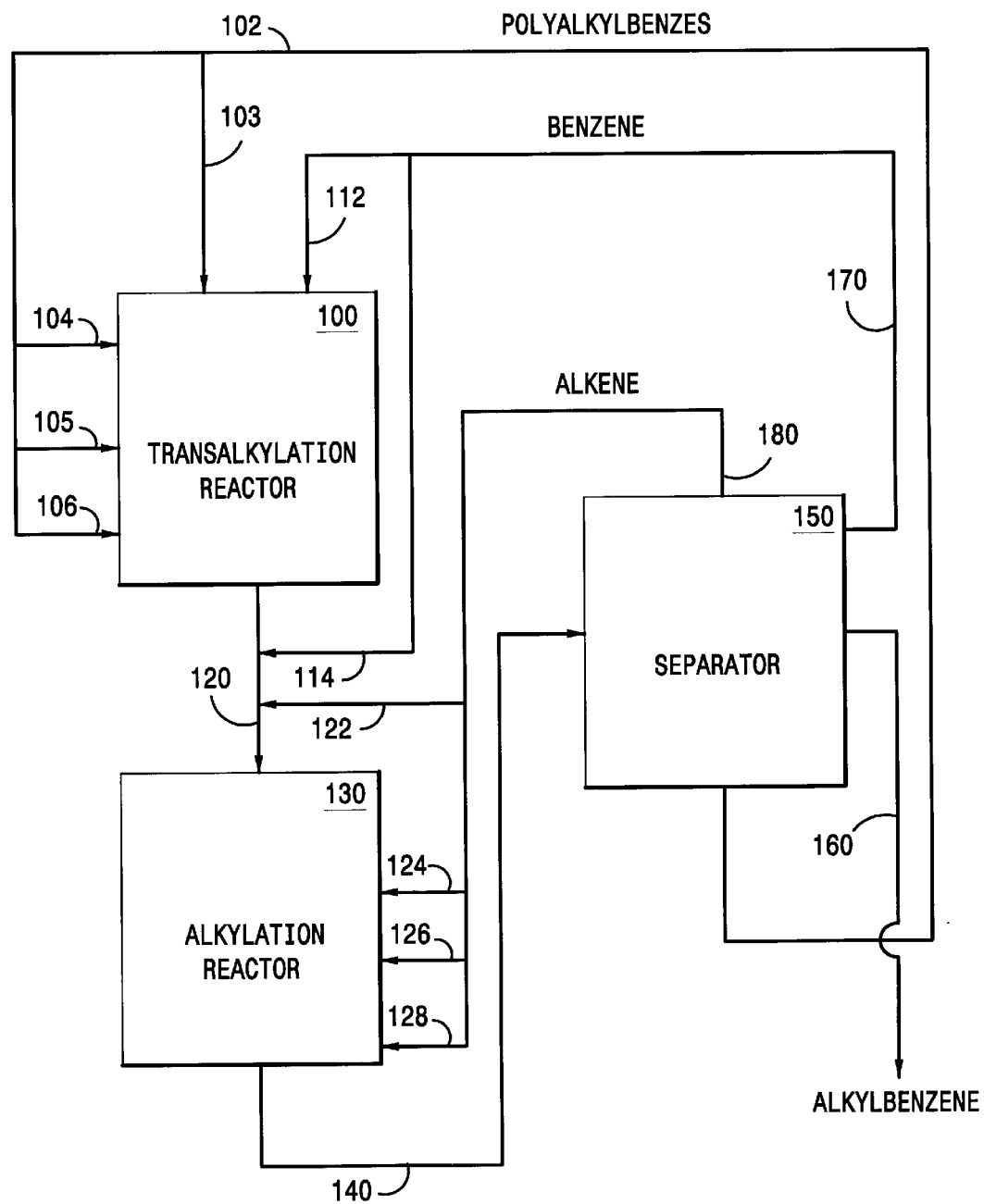
FIG. 1 is a diagrammatic representation of an embodiment of the present process, wherein separate transalkylation and alkylation reactors are used.

In accordance with the present process, the effluent from a transalkylation zone may be combined with fresh alkylating agent and cascaded directly (i.e., with no separation) to an alkylation zone. By proper design of the catalyst beds, both transalkylation and alkylation may also take place in the same reactor vessel.

The present process is particularly adapted to produce either ethylbenzene or cumene. When ethylbenzene is produced, benzene is alkylated with ethylene, and polyethylbenzenes are transalkylated with benzene. When cumene is produced, benzene is alkylated with propylene, and polypropylbenzenes are transalkylated with benzene. The polyalkylbenzenes (i.e., polyethylbenzenes and polypropylbenzenes) include the para, meta and ortho isomers of diethylbenzenes and diisopropylbenzenes, as well as trialkylbenzenes and tetraalkylbenzenes. Optionally, the polyalkylbenzenes containing three or more alkyl substituents (e.g., triethylbenzenes) may be removed from the feedstream to the transalkylation zone, such that the polyalkylbenzenes in the feedstream to the transalkylation zone consist essentially of dialkylbenzenes.

The feed to the transalkylation zone has a molar ratio of benzene to polyalkylbenzene of greater than one. For example, this molar ratio of benzene to polyalkylbenzene may be from 1.5 to 20, e.g., from 2 to 10. When one or more of these reactants is introduced into the transalkylation zone in multiple stages, the sum total of the multiply introduced reactant should be used to calculate the above-mentioned molar ratios.

In one preferred embodiment, the reactive components of the feed to the transalkylation zone consist essentially of benzene and polyalkylbenzenes. There may be minor amounts of other compounds which may be reactive or potentially reactive under the conditions of the transalkylation zone. For example, the feed may contain minor amounts, e.g., less than 10 wt % of other aromatics, such as monoalkylaromatics, e.g., ethylbenzene, cumene, n-propylbenzene or butylbenzenes, present as impurities or produced as unintended by-products.

In an alternative embodiment, the feed to the transalkylation zone may also contain part of the total effluent from the alkylation zone, excluding any unreacted alkene, as a recycle stream to provide a diluent to assist in controlling exotherm during the subsequent alkylation reaction.

The feed to the transalkylation zone is essentially free of both ethylene and propylene. These olefins are not intentionally added to the feed to the transalkylation zone. The effluent from the alkylation zone, including unreacted olefins, unreacted benzene and polyalkylbenzene by-product, may be subjected to a distillation step, prior any recycle, particularly of benzene and polyalkylbenzene, into the transalkylation zone. This distillation step is very effective in removing unreacted ethylene and propylene from the recycle stream. Accordingly, if there are any detectable levels of ethylene and propylene in the feed to the transalkylation zone, these olefins will be detectable only in trace quantities, e.g., in amounts less than 100 ppm.

The transalkylation zone comprises a transalkylation catalyst. Particularly, preferred catalysts comprise acidic solid oxides. Examples of such acidic solid oxides include aluminosilicates and materials, such as SAPO's, which contain elements other than silicon and aluminum. These acidic solid oxides may be amorphous or crystalline materials. These crystalline materials may have a non-layered, 3-dimensional framework structures, or layered structures, such as the layered structures of clays. Preferred acidic solid oxides are zeolites, particularly, medium-pore and large-pore size zeolites. Other examples of acidic solid oxides, include super acids formed by modifying zirconia with tungstates or sulfates.

In the transalkylation zone, the feed is contacted under conditions sufficient to produce monoalkylbenzene by a transalkylation reaction of benzene with polyalkylbenzene. Since the feed to the transalkylation zone includes a molar excess of benzene, the effluent from the transalkylation zone includes unreacted benzene in addition to monoalkylbenzene product.

The transalkylation zone may be confined in a single reactor which is separate from the reactor encompassing the alkylation zone. Alternatively, however, the transalkyation zone and the alkylation zone may be included in separate beds of a single reactor.

Various types of transalkylation reactors can be used. For example, the transalkylation reactor may be a fixed-bed reactor operating in an upflow or downflow mode or a moving-bed reactor operating with cocurrent or countercurrent catalyst and hydrocarbon flows. The transalkylation reactor may contain a single catalyst bed or multiple beds and may be equipped for the interstage addition of polyalkylbenzenes and/or benzene. The transalkylation reactor may be further equipped for interstage cooling. A moving-bed reactor makes possible the continuous removal of spent catalyst for regeneration and replacement by fresh or regenerated catalyst. Optionally, more than one transalkylation reactor may be used.

The transalkylation conditions may be liquid phase conditions, vapor phase conditions or mixed liquid/vapor phase conditions. The particular conditions, e.g., of temperature and pressure, are dependent, at least in part, on the nature of the transalkylation catalyst.

The entire effluent from the transalkylation zone is passed directly (i.e., cascaded) without separation into the alkylation zone. As a separate feed to the alkylation zone, there is also fed an olefin (i.e., ethylene or propylene) alkylating agent. The olefin cofeed may be introduced at any appropriate point. For example, when separate reactors are used, olefin may be injected into a line connecting a transalkylation reactor to an alkylation reactor. When a single reactor is used, olefin may be introduced between stages of a multiple bed reactor, wherein the bed upstream of the point of olefin injection comprises a transalkylation catalyst and the bed downstream of the point of injection comprises an alkylation catalyst. The olefin may also be first introduced into the alkylation reactor from a line separate from the line introducing the transalkylation reactor effluent into the alkylation reactor.

Whatever means are used to establish the first contact of olefin alkylating agent with the effluent of the transalkylation zone, it is preferred to introduce olefin at multiple stages as the reactants pass through the alkylation zone. The first point of introduction of the olefin alkylating agent is downstream from the transalkylation zone.

The effluent from the alkylation zone comprises the required monoalkylbenzene product, which is then separated from the other components of the effluent and recovered. Polyalkylbenzenes are separated from the effluent stream and recycled back to the transalkylation zone. Benzene separated from the alkylation zone effluent is recycled to transalkylation zone and/or the alkylation zone, whereas unreacted alkene is recycled to the alkylation zone. In addition, part of the total effluent from the alkylation zone, excluding any unreacted alkene, may be a recycled back to the alkylation zone to provide a quench stream to assist in controlling exotherm during the alkylation reaction.

The alkylation catalyst may be selected from the same general class of materials used for the transalkylation catalyst. Particularly, preferred catalysts comprise acidic solid oxides. Examples of such acidic solid oxides include aluminosilicates and materials, such as SAPO's, which contain elements other than silicon and aluminum. These acidic solid oxides may be amorphous or crystalline materials. These crystalline materials may have a non-layered, 3-dimensional framework structures, or layered structures, such as the layered structures of clays. Preferred acidic solid oxides are zeolites, particularly, medium-pore and large-pore size zeolites. Other examples of acidic solid oxides, include super acids formed by modifying zirconia with tungstates or sulfates.

The same catalyst may be used in both the transalkylation zone and the alkylation zone of the present process.

Preferably, however, different catalysts are chosen for the two zones, so as to be tailored for the particular reactions catalyzed therein.

Particular examples of suitable medium pore zeolites for use herein are those having a Constraint Index of 2–12 (as defined in U.S. Pat. No. 4,016,218), including ZSM-5, ZSM-11, ZSM-12, ZSM-22, ZSM-23, ZSM-35, and ZSM-48.

ZSM-5 is described in detail in U.S. Pat. Nos. 3,702,886 and Re. 29,948.

ZSM-11 is described in detail in U.S. Pat. No. 3,709,979.

ZSM-12 is described in U.S. Pat. No. 3,832,449.

ZSM-22 is described in U.S. Pat. No. 4,556,477.

ZSM-23 is described in U.S. Pat. No. 4,076,842.

ZSM-35 is described in U.S. Pat. No. 4,016,245.

ZSM-48 is more particularly described in U.S. Pat. No. 4,234,231.

The large-pore zeolites, including those zeolites having a Constraint Index less than 2, are well known to the art and have a pore size sufficiently large to admit the vast majority of components normally found in a feed chargestock. The zeolites are generally stated to have a pore size in excess of 7 Angstroms and are represented by zeolites having the structure of, e.g., Zeolite Beta, Zeolite Y, Ultrastable Y (USY), Dealuminized Y (Deal Y), Mordenite, ZSM-3, ZSM-4, ZSM-18, and ZSM-20. A crystalline silicate zeolite well known in the art and useful in the present invention is faujasite. The ZSM-20 zeolite resembles faujasite in certain aspects of structure, but has a notably higher silica/alumina ratio than faujasite, as does Deal Y.

Zeolite ZSM-14 is described in U.S. Pat. No. 3,923,636.

Zeolite ZSM-20 is described in U.S. Pat. No. 3,972,983.

Zeolite Beta is described in U.S. Pat. Nos. 3,308,069, and Re. No. 28,341.

Low sodium Ultrastable Y molecular sieve (USY) is described in U.S. Pat. Nos. 3,293,192 and 3,449,070.

Dealuminized Y zeolite (Deal Y) may be prepared by the method found in U.S. Pat. No. 3,442,795.

Zeolite UHP-Y is described in U.S. Pat. No. 4,401,556.

Other acidic solid oxides, which may be used to catalyze either the present alkylation reaction or the present transalkylation reaction, include MCM-22, PSH-3, SSZ-25, MCM-36, MCM-49 and MCM-56.

MCM-22 and its use to catalyze the synthesis of alkylaromatics, including ethylbenzene, is described in U.S. Pat. Nos. 4,992,606; 5,077,445; and 5,334,795. PSH-3 is described in U.S Pat. No. 4,439,409. SSZ-25 and its use in aromatics alkylation is described in U.S. Pat. No. 5,149,894. MCM-36 is described in U.S. Pat. Nos. 5,250,277 and 5,292,698. U.S. Pat. No. 5,258,565 describes the synthesis of alkylaromatics, including ethylbenzene, using a catalyst comprising MCM-36. MCM-49 is described in U.S Pat. No. 5,236,575. The use of MCM-49 to catalyze the synthesis of alkylaromatics, including ethylbenzene, is described in U.S. Pat. Nos. 5,493,065 and 5,371,310. MCM-56 is described in U.S. Pat. No. 5,362,697. The use of MCM-56 to catalyze the synthesis of alkylaromatics including ethylbenzene is described in U.S. Pat. Nos. 5,557,024 and 5,453,554.

Other acidic solid oxides which may be used to catalyze the present alkylation and transalkylation reactions include SAPO's, and tungstate modified zirconia. SAPO's, i.e. silicoaluminophosphates, are described in U.S. Pat. Nos. 5,114,563 and 4,440,871. The use of tungstate modified zirconia to catalyze the synthesis of alkylaromatics including ethylbenzene is described in U.S. Pat. No. 5,563,311.

The solid acidic oxide material may be composited with another material which is resistant to the temperatures and other conditions employed in the process of this invention. Such materials include active and inactive materials and synthetic or naturally occurring zeolites as well as inorganic materials such as clays and/or oxides such as alumina, silica, silica-alumina, zirconia, titania, magnesia or mixtures of these and other oxides. The latter may be either naturally occurring or in the form of gelatinous precipitates or gels including mixtures of silica and metal oxides. Clays may also be included with the oxide type binders to modify the mechanical properties of the catalyst or to assist in its manufacture. Use of a material in conjunction with the solid acidic oxide, i.e., combined therewith or present during its synthesis, which itself is catalytically active may change the conversion and/or selectivity of the catalyst. Inactive materials suitably serve as diluents to control the amount of conversion so that products can be obtained economically and orderly without employing other means for controlling the rate of reaction. These materials may be incorporated into naturally occurring clays, e.g., bentonite and kaolin, to improve the crush strength of the catalyst under commercial operating conditions and function as binders or matrices for the catalyst. The relative proportions of finely divided solid acidic oxide material and inorganic oxide matrix vary widely, with the crystal content ranging from about 1 to about 90 percent by weight and more usually, particularly, when the composite is prepared in the form of beads, in the range of about 2 to about 80 weight percent of the composite.

Examples of particular embodiments regarding the present process are described hereinafter with reference to FIG. 1. FIG. 1 provides a diagramatic representation of an embodiment of the present process, wherein separate transalkylation and alkylation reactors are used.

In FIG. 1, polyalkylbenzenes are introduced into transalkylation reactor 100 via polyalkylbenzene recycle line 102. The flow of polyalkylbenzenes from polyalkylbenzene recycle line 102 to polyalkylbenzene introduction lines 103, 104, 105, and 106 may be monitored by valve means (not shown in FIG. 1). Introduction lines 103, 104, 105, and 106 are positioned for staged addition of polyalkylbenzenes into transalkylation reactor 100. Benzene is also introduced into transalkylation reactor 100 via benzene recycle line 170 through benzene introduction line 124. Although not shown in FIG. 1, it will be understood that the benzene introduction line 124 may intersect polyalkylbenzene introduction line 104 upstream of transalkylation reactor 100, such that both polyalkybenzenes and benzene are introduced into transalkylation reactor 100 through a single line rather than two separate lines as shown in FIG. 1.

The entire effluent from transalkylation reactor 100 passes through transfer line 120 and into alkylation reactor 130. Make up benzene is introduced into transfer line 120 through benzene introduction line 114 and alkene is introduced into transfer line 120 through alkene introduction line 122. Although FIG. 1 depicts one embodiment, wherein all three of the effluent from the transalkylation reactor, make up benzene and alkene are introduced into the alkylation reactor 130 together via a single line, it will be appreciated that these three components may be introduced into the alkylation reactor 130, individually, via separate lines. It will further be appreciated that alkene may, optionally, be introduced into the transfer line 120 upstream from the point of introduction of benzene into line 120 or alkene introduction line 122 may intersect benzene introduction line 114, such that alkene and benzene are introduced into transfer line 120 through the same line.

It is preferred to add alkene in stages to alkylation reactor 130. This staged addition is illustrated in FIG. 1 with reference to additional alkene introduction lines 124, 126 and 128. Preferably, cooling is provided between the separate alkene introduction stages.

The effluent from alkylation reactor 130 passes through transfer line 140 to separator 150. The separator 150 may comprise one or more distillation columns and associated equipment, such as flash tanks and heat transfer means. In separator 150, the effluent from the alkylation reactor 130 is separated into streams comprising a polyalkylbenzene stream, an alkylbenzene stream, a benzene stream and an alkene stream. The separator 150 may also include provision for periodic removal of heavy residues from the sytem. The polyalkylbenzene stream passes from the separator via polyalkylbenzene recycle line 102. The alkylbenzene product stream passes from the separator via product recovery line 160. The benzene stream passes from the separator via benzene recycle line 170. The alkene stream passes from the separator via alkene recycle line 180.

In an alternative embodiment (not shown), part of the total effluent from the alkylation reactor, excluding any unreacted alkene, is recycled back to the transalkylation reactor 100 for cascading into the alkylation reactor 130 or, more preferably, directly into the alkylation reactor 130 to provide a diluent to assist in controlling exotherm during the alkylation reaction.

It will be understood that the present invention may involve a different process scheme than that depicted in FIG. 1, wherein the separate transalkylation reactor 100 and alkylation reactor 130 are replaced by a single multiple bed reaction vessel, provided that the beds for conducting the alkylation reaction are placed downstream from the beds for conducting the transalkylation reaction, and further provided that the first point of introduction of alkene feed is at a point downstream from the beds for conducting the transalkylation reaction.

It will be understood that FIG. 1 demonstrates the general flow of reactants and products throughout the present process. However, it will be further understood that FIG. 1 should not be construed to limit the present process to any particular reactor configuration. As mentioned herein previously, the present alkylation reactor and the present cocurrent transalkylation reactor may each be a fixed-bed reactor operating in an upflow or downflow mode or a moving-bed reactor operating with cocurrent or countercurrent catalyst and hydrocarbon flows.

Fresh feeds, particularly fresh benzene and fresh alkenes, may be introduced at any convenient points (not shown) in the overall scheme depicted in FIG. 1. Upon start-up of the reaction system, fresh benzene may be introduced into transalkylation reactor 100 through line 104 in the absence of a polyalkylbenzene cofeed. Optionally, on start-up of the reaction system, benzene may bypass the transalkylation reactor 100 so as to be diverted from introduction line 104 into line 114. As polyalkylbenzenes are subsequently produced in the system, polyalkylbenzene introduction lines 103, 104, 105 and 106 may be opened simultaneously or sequentially to accommodate an increasing flow of polyalkylbenzenes into transalkylation reactor 130. As the flow of polyalkylbenzenes increases into the transalkylation reactor 100, an appropriate flow of benzene into the transalkylation reactor 100 may take place through benzene introduction line 112. Eventually, the system may reach a steady state of operation, wherein the flow of polyalkylbenzene into transalkylation reactor 100 is essentially constant and the amount of polyalkylbenzenes produced in the alkylation reactor 130 is essentially the same as the amount of polyalkybenzenes converted in the transalkylation reactor 100.

The transalkylation and alkylation reactions may take place under liquid phase conditions or vapor phase conditions or mixed liquid/vapor phase conditions. For example, one of these reactions may take place under liquid phase or mixed liquid/vapor phase conditions, while the other reaction takes place under vapor phase conditions. However, both reactions preferably take place under liquid phase conditions.

Particular conditions for carrying out the vapor phase alkylation of benzene with ethylene or propylene may include a temperature of from about 650 to 900° F. (343 to 482° C.), e.g., from about 700 to 850° F. (371 to 454° C.), a pressure of about atmospheric to about 3000 psig, e.g., from about 25 psig to about 450 psig, a WHSV based on ethylene or propylene of from about 0.5 to about 2.0 hr$^{-1}$ and a mole ratio of benzene to ethylene or propylene of from 1:1 to 30:1.

Liquid phase alkylation of benzene with ethylene may be carried out at temperatures between 300 and 650° F. (150 to 340° C.) usually in the range of 400 to 520° F. (205 to 270° C.).

Pressures during the liquid phase alkylation of benzene with ethylene may be as high as about 3000 psig (20875 kPa) although generally will not exceed 1000 psig (7000 kPa). The reaction may be carried out in the absence of hydrogen and accordingly the prevailing pressures are those of the reactant species. The space velocity may be from about 0.1 to 20 WHSV, based on the ethylene feed. Preferred space velocities for the liquid phase alkylation of benzene with ethylene include ranges, for example, from about 0.5 to about 3 WHSV, e.g., from about 0.75 to 2.0 WHSV, (ethylene). The ratio of the benzene to the ethylene in the alkylation reactor may be from 1:1 to 30:1 molar, normally about 5:1 to 20:1 molar, and in most cases from about 5:1 to 10:1 molar.

When benzene is alkylated with propylene to produce cumene, the reaction may also take place under liquid phase conditions including a temperature of up to about 250° C., e.g., up to about 150° C., e.g., from about 10 to 125° C.; a pressure of about 250 atmospheres or less, e.g., from about 1 to about 30 atmospheres; and an aromatic hydrocarbon weight hourly space velocity (WHSV) of from about 5 to about 250 hr$^{-1}$, from 5 hr$^{-1}$ to about 50 hr$^{-1}$. An example of a combination of reaction conditions includes a temperature of from about 10 to 150° C., a pressure of from about 1 to about 30 atmospheres, and a WHSV of from about 5 to about 50 hr$^-$. Another example of a combination of reaction conditions includes a temperature of from about 10 to 250° C., a pressure of from about 250 atmospheres, and a WHSV of from about 5 to about 250 hr$^-$.

Particular conditions for carrying out the vapor phase alkylation of benzene with propylene may include a temperature of from about 100 to 600° F. (38 to 316° C.), e.g., from about 250 to 500° F. (121 to 260° C.), a pressure of from about 50 psig to 1000 psig, e.g., 300 psig to 600 psig, a WHSV based on propylene of from about 0.1 to about 2.0 hr$^{-1}$ and a mole ratio of benzene to propylene of from 1:1 to 50:1.

Particular conditions for carrying out the liquid phase transalkylation of benzene with polyethylbenzenes may include a temperature of from about 150° C. to about 260° C., a pressure of 7000 kPa or less, a WHSV based on the weight of the total liquid feed to the reaction zone of from about 0.5 to about 2.0 hr$^{-1}$ and a mole ratio of benzene to polyethylbenzene of from 1:1 to 30:1.

Particular conditions for carrying out the vapor phase transalkylation of benzene with polyethylbenzenes may include a temperature of from about 260° C. to about 482° C., e.g., from about 370 to 450° C., a pressure of from about atmospheric to about 3000 psig, e.g., from about 50 to about 500 psig, a WHSV based on the weight of the total vapor feed to the reaction zone of from about 1 to about 50 hr$^{-1}$ and a mole ratio of benzene to polyethylbenzene of from about 1 to about 50.

Particular conditions for carrying out the liquid phase transalkylation of benzene with polypropylbenzenes may include a temperature of from about 100 to 600° F. (38 to 316° C.), e.g., from about 250 to 450° F. (121 to 232° C.), a pressure of from about 50 psig to 1000 psig, e.g., 300 psig to 600 psig, a WHSV based on the weight of the total liquid feed to the reaction zone of from about 0.1 to about 10 hr$^{-1}$ and a mole ratio of benzene to polypropylbenzene of from 1:1 to 50:1.

Particular conditions for carrying out the vapor phase transalkylation of benzene with polypropylbenzenes may include a temperature of from about 260° C. to about 480° C., e.g., from about 371 to 454° C.), a pressure of from about atmospheric to about 3000 psig, e.g., from about 50 to about 500 psig, less, a WHSV based on the weight of the total vapor feed to the reaction zone of from about 1 to about 50 hr$^{-1}$ and a mole ratio of benzene to polypropylbenzene of from 1:1 to 50:1.

EXAMPLE

A zeolite beta catalyst was prepared by mixing 65 wt % zeolite beta (on a dry weight basis) in the hydrogen form with 35 wt % pseudoboehmite alumina (on a dry weight basis) and with sufficient water to form an extrudable paste. The paste was thoroughly mixed and then extruded through a screw extruder into the form of 1/16" extrudates. The extrudates were dried and then heated up in flowing nitrogen to 900° F. (480° C.) and then held at that temperature for 3 hours. Then flowing air was introduced and the temperature was raised to 1000° F. (540° C.) and then held at that temperature for 6 hours. The extrudates were then cooled and this finished catalyst was used in the process evaluation described below.

An MCM-22 catalyst was prepared by mixing 65 wt % MCM-22 (on a dry weight basis) in the sodium form with 35 wt % psuedoboehmite alumina (on a dry weight basis) and sufficient water to form an extrudable paste. The paste was thoroughly mixed and then extruded through a screw extruder into the form of 1/16" extrudates. The extrudates were dried and then heated in flowing nitrogen to 1000° F. (540° C.) and then held at that temperature for 6 hours. Then, the extrudates were cooled to room temperature. The extrudates were humidified and then a solution of ammonium nitrate was used to reduce the sodium level of the extrudates to less than 500 ppmw. The extrudates were dried in flowing air and then heated up in flowing air to a temperature of 1000° F. (540° C.) and then held at that temperature for 6 hours. The extrudates were then cooled and this finished catalyst was used in the process evaluation described below.

Experiments were performed in which the effluent from a transalkylation step catalyzed by 0.5 gms of beta/Al$_2$O$_3$ described above was passed directly to an alkylation stage using 1.0 gms of MCM-22/Al$_2$O$_3$ described above. The feed to the transalkylation stage was a blend (nominally 3/1 wt/wt) of benzene/diethylbenzenes (5.0 gms/hr) while ethene (1.0 gms/hr) was fed either between the transalkylation/alkylation stages or directly to the transalkylation stage. The pressure was 500 psig while the transalkylation and alkylation reactors were nominally at 500° F. and 430° F., respectively. Results are shown below in Table 1.

TABLE 1

Cascade Transalkylation/Alkylation Results

| | Ethene Feed Location | | | | | |
|---|---|---|---|---|---|---|
| | Between Beds | | | To Transalkylation | | |
| Composition, wt % | Feed | Product | Delta | Feed | Product | Delta |
| Ethene | 16.67 | 0.07 | −16.59 | 16.67 | 0.16 | −16.51 |
| Benzene | 57.87 | 23.11 | −34.76 | 57.87 | 25.30 | −32.57 |
| EB | 0.10 | 45.03 | 44.93 | 0.10 | 42.22 | 42.12 |
| DiEB | 23.39 | 24.09 | 0.71 | 23.39 | 21.39 | −2.00 |
| TriEB | 1.79 | 5.86 | 4.07 | 1.79 | 6.78 | 4.99 |
| Other Aromatics | 0.17 | 1.77 | 1.60 | 0.17 | 3.82 | 3.65 |
| Other PON | 0.02 | 0.07 | 0.05 | 0.02 | 0.33 | 0.31 |
| EB Impurities | | 279 | | | 935 | |

In both cases, ethylbenzene was the primary product. However, undesirable side reactions appear to be minimized in the case where the alkylating agent (ethene) is fed between the transalkylation and alkylation stages. This is reflected by lower yields of other aromatics; paraffins, olefins, and naphthenes (PON); and EB impurities. Higher selectivities to monoalkylate are expected at higher feed benzene concentrations.

What is claimed is:

1. A process for producing an alkylbenzene selected from the group consisting of ethylbenzene and cumene, said process comprising the steps of:

(a) introducing a feed into a transalkylation zone, said feed comprising benzene and polyalkylbenzene selected from the group consisting of polyethylbenzenes and polypropylbenzenes, the molar ratio of benzene to polyalkylbenzene in said feed being in excess of one, said feed being essentially free of ethylene and propylene, wherein said transalkylation zone comprises a transalkylation catalyst;

(b) contacting said feed with said transalkylation catalyst under sufficient transalkylation conditions to produce an effluent from said transalkylation zone comprising monoalkylbenzene and benzene;

(c) introducing (i) the entire effluent from the transalkylation zone and (ii) an alkene selected from the group consisting of ethylene and propylene into an alkylation zone comprising an alkylation catalyst; and (d) contacting said effluent from said transalkylation zone and said alkene with said alkylation catalyst under sufficient alkylation conditions to produce an effluent from said alkylation zone comprising monoalkylbenzene and polyalkylbenzenes, wherein the point of first introduction of alkene is downstream from the transalkylation zone.

2. A process according to claim 1, wherein both of said alkylation and said transalkylation are conducted in the liquid phase.

3. A process according to claim 1, wherein said transalkylation catalyst is different from said alkylation catalyst.

4. A process according to claim 1, wherein said transalkylation catalyst and said alkylation catalyst each comprise an acidic solid oxide.

5. A process according to claim 3, wherein said transalkylation catalyst and said alkylation catalyst each comprise an acidic solid oxide selected from the group consisting of zeolite beta, ZSM-5, ZSM-12, MCM-22, MCM-36, MCM-49, MCM-56, MCM-58, faujasite, mordenite, and tungstate modified zirconia.

6. A process according to claim 1, wherein said transalkylation zone and said alkylation zone are in separate reactors.

7. A process according to claim 3, wherein said transalkylation zone and said alkylation zone are in the same reactor, said reactor comprising at least two catalyst beds, said alkylation catalyst and said transalkylation catalyst being in separate catalyst beds.

8. A process as claimed in claim 1 including the step of recycling the polyalkylbenzene from the alkylation zone effluent back to the transalkylation zone.

9. A process as claimed in claim 1 including the step of recycling part of the total effluent from the alkylation zone, apart from any unreacted alkene, back to the transalkylation zone or the alkylation zone.

* * * * *